(12) United States Patent
Koppert et al.

(10) Patent No.: US 11,215,579 B2
(45) Date of Patent: Jan. 4, 2022

(54) METHOD FOR CLEANING, CONDITIONING, CALIBRATION AND/OR ADJUSTMENT OF AN AMPEROMETRIC SENSOR

(71) Applicant: ProMinent GmbH, Heidelberg (DE)

(72) Inventors: Klaus Koppert, Mannheim (DE); Holger Schopf, Heilbronn (DE); Thomas Winkler, Karlsruhe (DE)

(73) Assignee: ProMinent GmbH, Heidelberg (DE)

( * ) Notice: Subject to any disclaimer, the term of this patent is extended or adjusted under 35 U.S.C. 154(b) by 317 days.

(21) Appl. No.: 16/429,312

(22) Filed: Jun. 3, 2019

(65) Prior Publication Data

US 2019/0376923 A1 Dec. 12, 2019

(30) Foreign Application Priority Data

Jun. 7, 2018 (DE) ..................... 10 2018 113 640.4

(51) Int. Cl.
| | |
|---|---|
| *G01N 27/416* | (2006.01) |
| *G01N 27/38* | (2006.01) |
| *G01N 27/404* | (2006.01) |
| *G01N 27/30* | (2006.01) |
| *G01N 33/18* | (2006.01) |

(52) U.S. Cl.
CPC ......... *G01N 27/38* (2013.01); *G01N 27/4045* (2013.01); *G01N 27/4163* (2013.01); *G01N 27/301* (2013.01); *G01N 33/182* (2013.01)

(58) Field of Classification Search
CPC ............ G01N 27/416; G01N 27/4161; G01N 27/4163; G01N 27/453; G01N 27/48; G01N 27/49; G01N 33/182; G01N 33/1826; G01N 33/184
See application file for complete search history.

(56) References Cited

U.S. PATENT DOCUMENTS

| | | | |
|---|---|---|---|
| 4,772,375 A | | 9/1988 | Wullschleger et al. |
| 5,098,547 A | * | 3/1992 | Bryan ................ G01N 33/0006 204/401 |
| 6,607,642 B1 | | 8/2003 | Kiesele et al. |
| 8,329,024 B2 | | 12/2012 | Henry |
| 8,815,077 B2 | | 8/2014 | Wohlrab et al. |
| 2011/0000797 A1 | | 1/2011 | Henry |

(Continued)

FOREIGN PATENT DOCUMENTS

| | | |
|---|---|---|
| DE | 19939011 C1 | 1/2001 |
| DE | 102009036012 A1 | 2/2011 |

(Continued)

OTHER PUBLICATIONS

EPO computer-generated English language translation of the Description section of EP 1293778 A1, patent published (Year: 2003).*

(Continued)

*Primary Examiner* — Alexander S Noguerola
(74) *Attorney, Agent, or Firm* — Paul & Paul

(57) ABSTRACT

A method for cleaning, conditioning, calibration, adjustment and conditioning of an amperometric sensor of a measuring device includes generating a conditioning agent in the measuring device, wherein either an oxidising agent which is reduced at the working electrode or a reducing agent which is oxidised at the working electrode is used as conditioning agent.

19 Claims, 4 Drawing Sheets

(56) References Cited

U.S. PATENT DOCUMENTS

Figure 1:
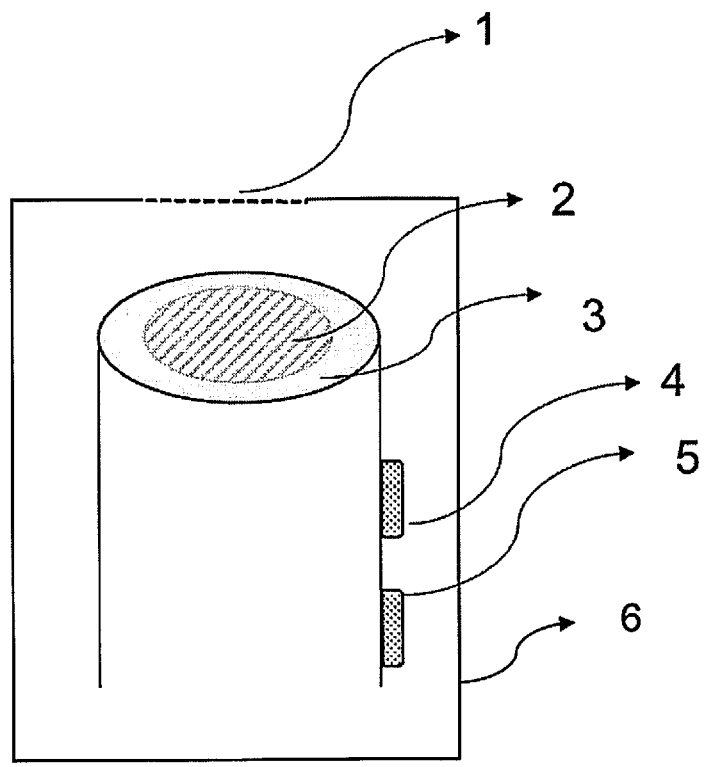

2012/0125790 A1 5/2012 Wohlrab et al.
2018/0120252 A1 5/2018 Hennings et al.

FOREIGN PATENT DOCUMENTS

| DE | 102011120819 A1 | 6/2013 |
|----|-----------------|--------|
| DE | 102016120581 A1 | 5/2018 |
| EP | 1293778 A2 | 3/2003 |

OTHER PUBLICATIONS

Analytical Technology, Inc. O & M Manual for Model Q46H-79PR Total Chlorine Monitor (Year: 2017).*
European Search Report, dated Nov. 22, 2019, European Application No. EP 19 177 266.4.

* cited by examiner

METHOD FOR CLEANING, CONDITIONING, CALIBRATION AND/OR ADJUSTMENT OF AN AMPEROMETRIC SENSOR

CROSS-REFERENCE TO RELATED APPLICATION

This application is claims the priority of German Application No. 102018113 640.4, filed on Jun. 7, 2018.

SUBJECT MATTER OF THE INVENTION

The invention relates to a method for cleaning, conditioning, calibration and/or adjustment of an amperometric sensor of a measuring device for determining a content substance in a sample, having a measuring chamber, sealed by a selectively permeable membrane, containing an electrolyte, in which the working electrode and a working reference electrode connected electrically with the working electrode are arranged, wherein the membrane is permeable to the content substance which is to be determined. The determination of the content substance takes place during a measuring interval in that a voltage is applied between the working electrode and working reference electrode, the current which flows via the electrical connection between working electrode and working reference electrode is measured and the content substance deduced from the measured current. The invention also relates to an amperometric sensor, a measuring device for carrying out the method according to the invention and the use of a conditioning agent.

BACKGROUND TO THE INVENTION

The result of electrochemical measuring methods for determining content substances in a sample often depends greatly on the active electrode surface of a sensor. However, operation leads over time to deposits and changes on the electrode which reduce the active electrode surface and as a result adversely affect the result of the measuring method. This leads in practice to a high expenditure of effort on cleaning and adjustment and there is a risk of uncertain and incorrect measured values.

For this reason, cleaning of the electrode at regular intervals is necessary. Different methods of doing so are known from the prior art.

Firstly, there is the possibility of mechanical cleaning, for example through abrasion with sand, corundum or similar hard materials. However, this method is laborious and cost-intensive and in most cases leads to unreliable measured values in measuring devices for contaminated samples. The apparatus also needs to be dismantled, at least in order to change the abrasive material.

A further possibility involves electrolytic degreasing. In this case an alkaline cleaner is added to the electrolyte and the electrodes are polarised alternatingly. The cleaning effect of the alkaline solution is reinforced by the development of gas on the electrode surface. However, this method has so far only been used to a very limited extent, because it is to be feared that the polarisation capability of the electrodes during the measurement is negatively influenced through the addition of the base.

A further possibility for cleaning is disclosed in the patent specifications CH 672845 A5 and EP 1452858 B1. In these, a method is described in which, in a cleaning section separate from measuring operation, a voltage of alternating polarity is applied to the working electrode and return electrode, so that both reducing and also oxidising gases are formed alternatingly at the working electrode and the return electrode. As a result, impurities are detached from the electrodes and the active electrode surfaces exposed. However, due to the gases released in the cleaning operation, the application of this method for membrane-covered sensors is ruled out.

In addition, in all of the aforementioned methods, the active electrode surface first needs to be conditioned following the cleaning operation, i.e. a measurement-capable surface must form through the establishment of equilibrium, so that a virtually constant blank value and a consistent sensitivity of the measured parameter, which is necessary for a reliable measurement, has become established. The conditioning behaviour is dependent on the concentration of the content substance which is to be determined in the sample. With a very low concentration of the content substance, the conditioning phase can take several hours to days.

A further problem which cannot be solved, or can only be solved inadequately, with the methods from the prior art arises if the concentration of the content substance to be measured lies below a threshold characteristic for the sensor type and thus only a very low current flow or at times no current flow at all occurs between the working electrode and the corresponding reference electrode ("zero sensor"). Over time this can lead to a change in the active electrode surface. In this case too the working electrode needs to be re-conditioned until the active electrode surface has formed again and meaningful measured values can be obtained.

In membrane-covered amperometric sensors, the measuring chamber is partially limited by a membrane which is selectively permeable to the content substance which is to be determined. This membrane is in direct contact with the sample which is to be measured. If, due to the absence of the content substance, the sensor is inactive over a longer period of time, deposits, in particular organic deposits such as biofilms, form on the membrane surface or within the pores of the membrane. This affects the diffusion of the analyte through the membrane to the working electrode and can then influence the sensitivity of the sensor as well as the accuracy of measurement. As a cost-generating maintenance step, the membrane cap which encloses the membrane needs to be changed regularly.

The commercially available measuring device W&T/Siemens Deox/2000® solves part of the aforementioned problems in that a conditioning agent is continuously fed into the measuring chamber from outside which is then converted at the working electrode. This keeps the electrode permanently in a measurement-capable state. The conditioning agent $I_2$ is produced in a reaction tube installed before the measuring chamber through the redox reaction of KI with chloramine T. The aqueous $I_2$ solution is then introduced into the measuring chamber by means of a peristaltic pump. In order to determine the concentration of a content substance in a sample, a defined quantity of sample is mixed with the $I_2$ solution before feeding it into the measuring chamber. The concentration of iodine is increased or lowered through reaction of the iodine with the oxidising or reducing content substance in the sample. This also changes the measured value of the amperometric sensor, as a result of which the concentration of the content substance which is to be determined can be deduced. However, this method requires not only the integration of a reaction tube in the measuring device, for continuous operation corresponding quantities of reactive and in some cases unstable chemicals such as chloramine T need to be kept in store. These can break down during the course of storage into undesired by-products which contaminate the sensor. Furthermore, the conditioning agent can only be changed in a complicated manner, namely by replacing the stored chemicals.

OBJECT

The object of the present invention is to provide a method for cleaning, conditioning, calibration and/or adjustment of a membrane-covered amperometric sensor of a measuring device for determining a content substance in a sample which exhibits a comparable or even a better cleaning and conditioning effect than the methods known from the prior art, for which a simpler equipment set-up is sufficient, in particular wherein no chemicals need to be kept in store, and which makes possible an extension of the service life of the membrane.

DESCRIPTION OF THE INVENTION

According to the invention, this object is achieved through a method of the aforementioned type, characterised in that it comprises the following steps:
  generating a conditioning agent at the working electrode and/or at a generator electrode arranged in the measuring device, wherein the conditioning agent is an oxidising or reducing agent,
  oxidising the conditioning agent at the working electrode, if the conditioning agent is a reducing agent, or reducing the conditioning agent at the working electrode, if the conditioning agent is an oxidising agent.

Through the electrochemical conversion of the conditioning agent, the working electrode is cleaned and left in a measurement-capable state with an active electrode surface, so that a virtually constant blank value and a consistent sensitivity of the measured parameter, which are necessary for a reliable measurement, become established. If the working electrode is already in a measurement-capable state, this is maintained in this state through the electrochemical conversion of the conditioning agent.

Without being tied to the theory, the inventors assume that the conditioning of the working electrode takes place through a removal of deposits and a depolarisation.

According to the invention, the conditioning agent can be generated at a generator electrode arranged in the measuring device, preferably in the measuring chamber, and/or at the working electrode arranged in the measuring chamber. If the conditioning agent is generated at a generator electrode arranged in the measuring device from a reducing or oxidising agent contained in the electrolyte, the conditioning agent reaches the working electrode arranged in the measuring chamber through diffusion and/or transport through a pump and can be converted there through application of a voltage necessary for conversion. As a result, the conditioning effect is achieved. The generation of the conditioning agent can take place during a measuring interval or in a separate conditioning interval. Preferably, the conditioning agent is converted back into the oxidising or reducing agent contained in the electrolyte. Alternatively or additionally, the conditioning agent can also be generated at the working electrode. In this case the generation of the conditioning agent can only take place in a separate conditioning interval, i.e. the measurement of the content substance must be paused and the conditioning agent generated from a reducing or oxidising agent contained in the electrolyte through application of a corresponding voltage between working electrode and working reference electrode. The electrochemical redox reaction can then be reversed through a change in the voltage, i.e. the conditioning agent is no longer generated at the working electrode, but converted. As a result, the conditioning effect begins. Preferably, the conditioning agent is converted back into the oxidising or reducing agent contained in the electrolyte.

The method according to the invention also allows the further components of the amperometric sensor, in particular the membrane and the further electrodes, to be freed of impurities which affect the diffusion and the electrochemical reaction at the working electrode or delays the deposit of impurities. This is attributable to the oxidative or reductive effect of the conditioning agent, which can be dispersed in the electrolyte through diffusion.

The "measuring device" is the spatially limited container which comprises the at least one amperometric sensor and a control device. It can also contain one or more spatially limited modules for throughflow regulation, for the measurement of the pH value and a module with at least one generator electrode as well as one or more pumps. The amperometric sensor can be connected with the further modules, if provided, via one or more connections which contain electrolyte. The content substances in the sample and/or the conditioning agent can be transported to the measuring chamber via pumps. At the same time, or alternatively, the content substances and/or the conditioning agent can reach the measuring chamber through diffusion. In this case they diffuse through the membrane and are converted within the measuring chamber at the working electrode.

The amperometric sensor comprises a measuring chamber which contains electrolyte and in which the working electrode and a working reference electrode connected electrically with the working electrode are arranged. In the context of the invention, a "working electrode" is the electrode which is used to determine the measured value of the amperometric sensor. The content substance of the sample which is to be determined is oxidised or reduced electrochemically at this electrode. For this purpose, during the measuring operation a voltage is applied between the working electrode and the reference electrode connected electrically with this, wherein the processes are controlled using a suitable arrangement, for example a potentiostat.

The determination of the content substance during a measuring interval is effected in that the current which flows via the electrical connection between working electrode and working reference electrode is measured and the content substance deduced from the measured current.

In one embodiment, the amperometric sensor also includes a working return electrode, which is also connected electrically with the working reference electrode, and at which a redox reaction takes place for charge balancing. A corresponding embodiment of the working electrode system is referred to as a three-electrode arrangement. In a preferred embodiment, the working reference electrode can also simultaneously be the working return electrode. This embodiment is referred to as a two-electrode arrangement.

In the context of the present invention, the term "electrolyte" covers ion-conducting media, in particular ion-conducting fluids, for example saline solutions or saline gels.

The measured value of the amperometric sensor is the current strength which is measured between the working electrode and the working reference electrode.

The "sample" of which the content substance is to be determined is a fluid, preferably an ion-conducting fluid, for example water.

In one embodiment, the working electrode consists of a precious metal, preferably platinum or gold, particularly preferably platinum. In another embodiment, the working electrode consists of glassy carbon or other electrode materials known in the literature.

The "conditioning agent" which is generated in the measuring device and reduced at the working electrode of the amperometric sensor can be an oxidising agent. In this context, oxidising agent means that the redox pair consisting of oxidising agent and the corresponding reducing agent has a redox potential, so that the oxidising agent is reduced to the corresponding reducing agent through the voltage applied to the working electrode, i.e. the voltage between the working electrode and the electrically connected working reference electrode is less than the standard redox potential of the redox pair consisting of oxidising agent and the corresponding reducing agent.

If the conditioning agent is for example $I_2$, then under standard conditions the working electrode must be polarised by <540 mV in relation to the working reference electrode, since the standard redox potential of the redox pair is $I_2/2I^-$ 540 mV. If the voltage lies below this limit value, iodine is reduced to iodide:

$$I_2 + 2e^- \rightarrow 2I^-$$

If not working under standard conditions, then the applied voltage must be adjusted accordingly, as the skilled person knows. Among other things, the known overvoltages for different electrode materials must be taken into consideration. The conditioning agent which is generated in the measuring device can also be a reducing agent. In this context reducing agent means that the redox pair consisting of the reducing agent and the corresponding oxidising agent has a redox potential, so that the reducing agent is oxidised into the corresponding oxidising agent through the voltage applied at the working electrode.

In a preferred embodiment of the invention, the conditioning agent is generated at the generator electrode. In the context of the invention, a "generator electrode" is an electrode used for the electrolytic generation of one or more conditioning agents in the measuring device. For this purpose, a voltage is applied between the generator electrode and a generator reference electrode connected with this at such a level that a conditioning agent is generated from a reducing or oxidising agent which is contained in the electrolyte. For this purpose, the potential between the generator electrode and the generator reference electrode is controlled using a suitable arrangement, for example a potentiostat. In one embodiment, the measuring device also includes a generator return electrode, which is also connected electrically with the generator reference electrode, and at which a redox reaction takes place for charge balancing. A corresponding embodiment of the generator electrode system is referred to as a three-electrode arrangement. In a preferred embodiment, the generator reference electrode can also simultaneously be the generator return electrode. This embodiment is referred to as a two-electrode arrangement. The working electrode arranged in the measuring chamber and the generator electrode arranged in the measuring device can have one and the same reference electrode. Also preferably, the working electrode and generator electrode have one and the same return electrode. The shared use of electrodes allows the number of electrodes in the measuring device to be reduced accordingly. For example, the total number of electrodes, which in a three-electrode arrangement of the working electrode system and a three-electrode arrangement of the generator electrode system amounts to 6, can be reduced to 4 through shared use of the same reference and return electrodes.

In one embodiment, the generator electrode consists of a precious metal, preferably platinum or gold, particularly preferably platinum. In another embodiment, the working electrode consists of glassy carbon.

In a further preferred embodiment, the generator electrode consists of titanium.

The generator electrode can for example generate $I_2$ as conditioning agent. For this purpose, the electrolyte must contain the corresponding reducing agent, iodide, and the generator electrode must be polarised by >540 mV in relation to the generator reference electrode, since the standard redox potential of the redox pair amounts to $I_2/2I^-$ 540 mV. If this limit value is exceeded, iodide is oxidised into iodine:

$$2I^- \rightarrow I_2 + 2e^- \qquad \text{generator electrode reaction}$$

The generated conditioning agent iodine then diffuses to the working electrode. If this is polarised by <540 mV in relation to the working reference electrode, then iodine is there reduced to iodide again, as a result of which the conditioning effect occurs.

$$I_2 + 2e^- \rightarrow 2I^- \qquad \text{working electrode reaction}$$

In order that a conditioning agent can be generated at the generator or working electrode, the electrolyte must contain the reducing or oxidising agent, corresponding to the conditioning agent, from which the conditioning agent is generated, in sufficient concentration. This can for example be achieved in that the electrolyte contained in the measuring device is a saline solution, for example of a metal iodide salt.

The conditioning agent can also be generated in that a reducing or oxidising agent is generated at the generator electrode which can reduce or oxidise an oxidising/reducing agent contained in the electrolyte into the conditioning agent.

If the conditioning agent is for example to be $I_2$, then this can also be generated in the measuring device in that the electrolyte contains iodide ions and an oxidising agent is generated in the measuring device at the generator electrode which can oxidise iodide into $I_2$.

If the oxidising agent is for example $Br_2$, then this is reduced from $I^-$ under standard conditions and the conditioning agent $I_2$ is obtained:

| | |
|---|---|
| $Br_2 + 2e^- \rightarrow 2 Br^-$ | reduction |
| $2 I^- \rightarrow I_2 + 2 e^-$ | oxidation |
| $Br_2 + 2 I^- \rightarrow 2 Br^- + I_2$ | total |

As a result of the reaction, $I_2$ is produced which, as described above, is reduced through the application of corresponding voltage at the working electrode. The conditioning effect is achieved through the reaction at the working electrode.

Preferably, the conditioning agent is an oxidising agent, particularly preferably bromide, chlorine, iodine, most preferably iodine.

The conditioning agent generated through the working electrode or through the generator electrode or the corresponding oxidising/reducing agent can pass through the pores or through the material of the membrane. The deposit of substances, in particular organic deposits such as biofilms, on the surface or within the pores of the membrane can be delayed or reduced through oxidation or reduction of the substance. In this way, the service life of the membrane can be significantly extended.

In one embodiment of the invention, the conditioning agent is generated at the generator electrode during the measuring interval. In this case the reference value which is produced at the working electrode through the fed or generated conditioning agent is to be subtracted from the measured value of the amperometric sensor.

This allows a continuous measuring operation to be guaranteed, i.e. the electrode surface of the working electrode remains active and no cleaning and/or conditioning phases are necessary.

In a further embodiment of the invention, the conditioning agent is generated at the working electrode or at the generator electrode in a separate cleaning and/or conditioning operation. It is advantageous that the conditioning behaviour of the electrodes is dependent on the concentration of the conditioning agent. The conditioning phase can be shortened through the generation of a correspondingly high concentration of conditioning agent.

In a further embodiment, the conditioning agent is generated discontinuously, preferably in a pulsed manner, wherein the time interval at which the conditioning agent is generated is very much shorter than the time interval during which no conditioning agent is generated. If the conditioning agent is generated at the generator electrode during the measuring operation, then the reference value which is produced at the working electrode through the conditioning agent is to be subtracted from the measured value of the sensor. Alternatively, the measurement for is also paused for the short time interval during which the conditioning agent is generated.

In one embodiment of the invention, the conditioning agent is generated continuously. If the continuous generation takes place at the generator electrode during the measuring interval, a defined, virtually constant reference value is, through the conditioning agent, obtained at the working electrode, which is to be subtracted from the measured value of the working electrode. As a result of the continuous generation of the conditioning agent, a consistent cleaning and conditioning effect is then achieved. This prevents impurities from being able to build up on the surface of the working electrode and change the structure of the electrode surface of the working electrode in such a way that it becomes inactive. Consequently, the total amount of conditioning agent which is generated at the generator electrode can be kept low.

In a preferred embodiment, a predetermined quantity of conditioning agent is generated in the measuring device.

In one embodiment of the invention, the conditioning agent which is generated is the content substance of the sample which is determined by the amperometric sensor. This can advantageously be used to determine the content substance of a sample the concentration of which lies below the detection limit of a sensor in which no conditioning agent is fed into the measuring chamber or generated therein:

The detection limit of a sensor refers to the value of a measuring method up to which the measured variable can still just be reliably measured.

The measured value at the detection limit has an increased inaccuracy which does not however exceed a predetermined statistical confidence interval. Measured values which have a greater inaccuracy than the predetermined interval lie below the detection limit and are described as being unmeasurable or undetectable in terms of measuring technology.

The criterion of "reliable detection" is as a rule related to the precision of the measuring method in an empty measurement producing the blank value. This means the statistical error or the fluctuation of the measuring signal if no sample is present (e.g. the standard deviation from the blank value).

In the context of the invention, a measurement counts as proof if the measured value lies at least three standard deviations above the blank value.

In order to determine the content substance of a sample the concentration of which lies below the detection limit of a measuring device in which no conditioning agent is generated in the measuring device, the content substance which is to be determined is generated in the measuring device at the generator electrode during the measurement, or before the measurement at the working electrode. During conversion at the working electrode, a measured value is obtained as the sum of the reference value which is generated at the working electrode through the conditioning agent and the value which is generated at the working electrode through the content substance of the sample. In this way, the measured value obtained can be raised to a value above the detection limit. The content substance in the electrolyte can be determined through subtraction of the reference value from the measured value.

In a further embodiment of the invention, the conditioning agent which is generated at the working electrode or generator electrode is not the content substance which is determined by the amperometric sensor. In a further embodiment, several different oxidising and/or reducing agents can be generated at the generator electrode or working electrode. It is advantageous in the method according to the invention that the conditioning agent can be changed very quickly. If the electrolyte already contains different corresponding oxidising or reducing agents, a change can already be effected by adapting the voltage at the working electrode or generator electrode. The conditioning agent can also be changed in that a corresponding oxidising or reducing agent which is not already contained therein is added to the electrolyte and the voltage at the working electrode or generator electrode is adjusted such that this is converted into the conditioning agent.

In one embodiment, a detection electrolyte is used as electrolyte. A detection electrolyte contains a component which is reduced or oxidised into a detection component through the content substance of the sample which is to be determined. The detection component is oxidised or reduced at the working electrode and the content substance which is to be determined is deduced on the basis of the measured current strength. If for example an iodide salt solution is used as detection electrolyte in a measuring device for the determination of $Cl_2$ in a sample, then the content substance which is to be determined in the sample, $Cl_2$, oxidises the $I^-$ contained in the detection electrolyte into the detection component $I_2$.

| | |
|---|---|
| $Cl_2 + 2e^- \rightarrow 2\ Cl^-$ | reduction |
| $2\ I^- \rightarrow I_2 + 2\ e^-$ | oxidation |
| $Cl_2 + 2\ I^- \rightarrow 2\ Cl^- + I_2$ | total |

The detection component $I_2$ can then be reduced at the working electrode and the content substance $Cl_2$ deduced via the current strength obtained as measured value.

In a preferred embodiment, the detection component is used as conditioning agent.

In a preferred embodiment, the content substance of the sample which is to be determined is an oxidising agent which is reduced at the working electrode, for example oxidative halogen compounds such as those of chlorine, bromine and iodine, chloramines and bromamines, $Cl_2$, $Br_2$, $O_3$, $ClO_2$, peracetic acid, $H_2O_2$, a chlorite or hypochlorite salt or the corresponding acids, preferably hypochlorous acid (HOCl).

In a preferred embodiment, the electrolyte is an iodide salt solution and the conditioning agent $I_2$.

In a preferred embodiment, the method according to the invention is used to monitor the functionality of the sensor. For this purpose, a defined quantity of the content substance which is to be determined is generated at the generator electrode and a voltage applied between working electrode and working reference electrode and the current which flows via the electrical connection between working electrode and working reference electrode is measured and compared with a known value. In this way, any faults such as a sensor defect, cable breaks or errors in the evaluating system can be detected.

In a preferred embodiment, an adjustment value is deducted from the current value measured during the measuring interval, wherein the adjustment value is determined in that, during an adjustment interval in which no content substance of a sample which is to be determined is present in the electrolyte, a defined quantity of the content substance which is to be determined is generated at the generator electrode and a voltage applied between working electrode and working reference electrode and the current which flows via the electrical connection between working electrode and working reference electrode is measured.

In a further preferred embodiment, the conditioning agent within the measuring chamber is generated through the generator electrode. It is particularly advantageous to operate the generator electrode as the anode if the working electrode is used as the cathode, and to operate the generator electrode as the cathode if the working electrode is used as the anode.

The invention also comprises an amperometric sensor for carrying out the method defined above, wherein the sensor comprises at least one working electrode arranged in a measuring chamber containing the electrolyte, a working reference electrode and a selectively permeable membrane which limits the measuring chamber, wherein a generator electrode and a generator reference electrode are arranged in the measuring chamber and wherein a control device is provided with which a measuring voltage can be applied between working electrode and working reference electrode and with which a generator voltage can be applied between generator electrode and generator reference electrode.

In the method according to the invention, the direction of diffusion of the conditioning agent results from its concentration gradient. In one embodiment of the invention, the conditioning agent is generated at a generator electrode arranged in the measuring device. The concentration of the conditioning agent is high at the generator electrode, since it is generated there from the corresponding oxidising/reducing agent. At the working electrode, the conditioning agent is, in contrast, converted, so that the concentration there is normally lower. As a rule, where the generator electrode is arranged outside of the measuring chamber the conditioning agent therefore flows into this and is converted there. However, if the generator electrode is arranged within the measuring chamber, the concentration is generally lowest outside of the measuring chamber. The conditioning agent generated at the generator electrode flows out of the measuring chamber, for the most part through the permeable membrane, and can therefore not act as a conditioner. If the generator electrode is arranged within the measuring chamber, it is therefore advantageous to arrange the working electrode in the direction of diffusion of the conditioning agent in order to maximise the cleaning and conditioning effect of the conditioning agent. If the working electrode is arranged in this direction, the conditioning agent is oxidised or reduced here, before passing out of the membrane, into the corresponding reducing or oxidising agent, which then diffuses back to the generator electrode. Consequently, a closed circuit is formed, as a result of which virtually no oxidising or reducing agent can diffuse out of the membrane.

In order to achieve such an arrangement of working electrode and generator electrode, in one embodiment the working electrode can have at least one cylindrical section and the generator electrode a hollow cylindrical section, wherein the working electrode is arranged with its cylindrical section within the hollow cylindrical section of the generator electrode. Preferably, the working electrode is arranged within the hollow cylindrical section of the generator electrode in such a way that both base surfaces of the working electrode and generator electrodes pointing towards the selectively permeable membrane lie flush with one another or the base surface of the generator electrode is arranged at a greater distance from the selectively permeable membrane than the base surface of the working electrode. The result of this is that the conditioning agent which is generated at the generator electrode is oxidised or reduced at the working electrode and only diffuses through the membrane to the outside to a small extent.

Preferably, the effective surface of the selectively permeable membrane, i.e. the permeable surface, is smaller than or equal to the base surface of the working electrode facing the membrane. The result of this is that the direction of flow of the conditioning agent generated at the generator electrode has a component pointing radially inwards, i.e. towards the working electrode, consequently the conditioning agent diffuses towards this, and is reduced or oxidised there.

In a particularly preferred variant of this embodiment, the working electrode is arranged as follows in the direction of diffusion of the conditioning agent:

The working electrode is cylindrical and the generator electrode hollow cylindrical in form, wherein the working electrode, with a smaller diameter, is arranged within the hollow cylinder of the generator electrode. On the side facing the membrane, the base surfaces of the two cylinders lie flush with one another. The selectively permeable section of the membrane is smaller than the base surface of the cylinder of the working electrode and is arranged such that its projection on the base surface of the working electrode lies at least 90% on the base surface of the working electrode. Preferably, the selectively permeable section of the membrane is arranged concentrically to the base surface of the cylinder of the working electrode. FIG. 1 shows an apparatus which is suitable for carrying out such a preferred method.

The invention also comprises a measuring device for carrying out the method defined above, wherein the device has at least one amperometric sensor and a control device, as well as at least one generator electrode arranged in the measuring device. With the control device, a measuring voltage can be applied between working electrode and working reference electrode and a generator voltage can be applied between generator electrode and generator reference electrode, the level of which can be different from or equal to the measuring voltage, but the polarity of which is opposite.

Figure 2:
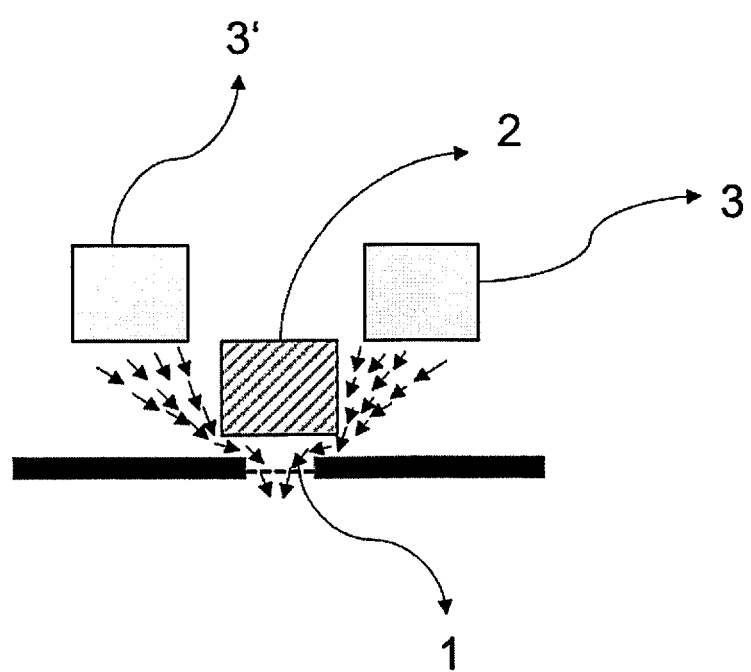

The attached figures represent special embodiments of the invention, wherein:

FIG. 1: shows a schematic representation of a special embodiment of a measuring chamber according to the invention with selectively permeable membrane and FIG. 2: shows a schematic representation of a section of a special embodiment of a measuring chamber according to the invention with selectively permeable membrane and generator electrodes arranged therein.

Figure 3:
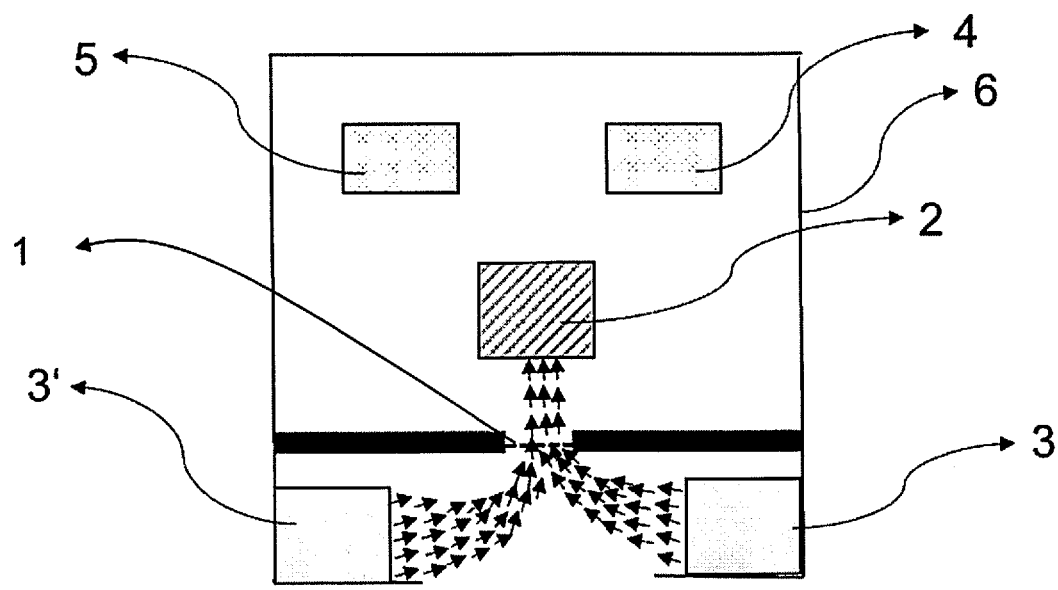

FIG. 3: shows a schematic representation of a special embodiment of a measuring device according to the invention with a measuring chamber with selectively permeable membrane and generator electrodes arranged in physical proximity to the measuring chamber.

Figure 4:
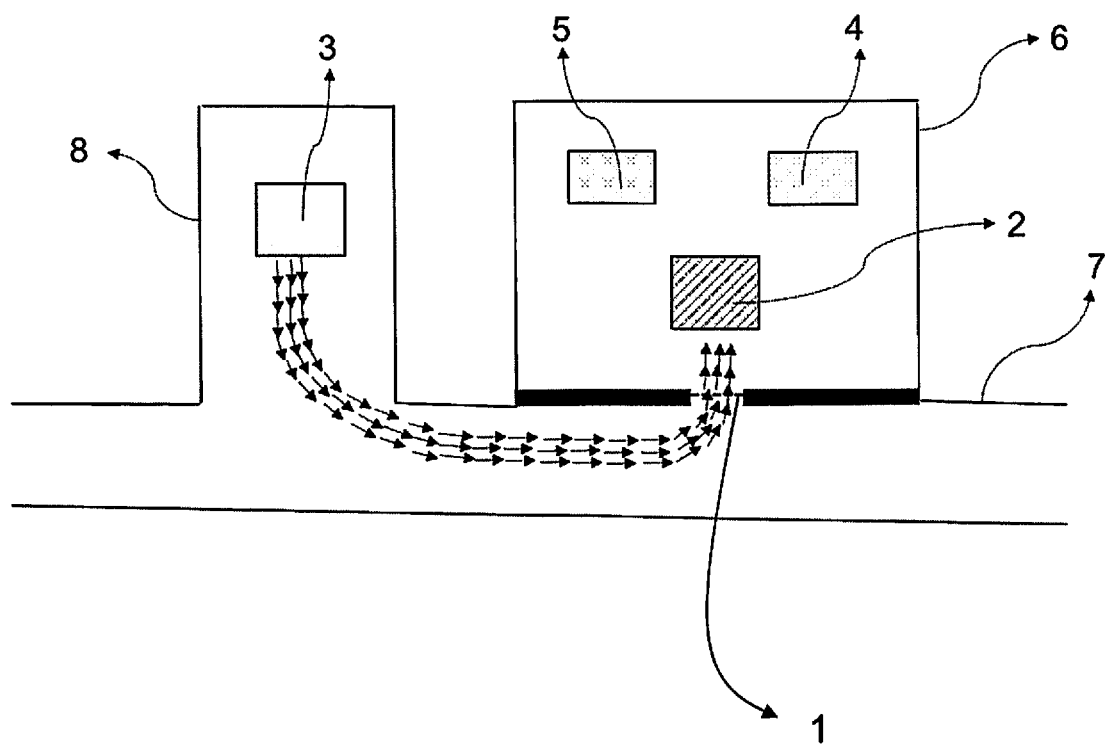

FIG. 4: shows a schematic representation of a special embodiment of a measuring device according to the invention with a measuring chamber with selectively permeable membrane and a separate module which contains the generator electrode.

FIG. 1 shows a schematic representation of a measuring chamber 6 of an amperometric sensor according to the invention which has a selectively permeable membrane 1, a working electrode 2, a generator electrode 3 and the associated reference or return electrodes 4 and 5. The working electrode 2 and generator electrode 3 are cylindrical in form with different diameters, wherein the working electrode, with a smaller diameter, is formed within the hollow cylindrical generator electrode. The base surfaces of the working electrode and generator electrodes facing the selectively permeable membrane lie flush with one another, wherein the projection of the effective surface of the membrane only lies on the base surface of the working electrode and is smaller than the base surface of the working electrode.

FIG. 2 shows a section from the representation of a special embodiment of an amperometric sensor according to the invention, with a selectively permeable membrane 1, a working electrode 2 and generator electrodes 3, 3'. The working electrode is arranged at a shorter distance from the effective surface of the selectively permeable membrane than the generator electrodes and the effective surface of the membrane is smaller than the surface of the working electrode pointing towards the effective surface. The two surfaces are also concentric in form. The section also shows the flow vectors of the conditioning agent formed at the generator electrode. The working electrode is arranged in the direction of diffusion of the conditioning agent. This increases the cleaning and conditioning effect of the oxidising or reducing agent.

FIG. 3 shows, schematically, a special embodiment of a measuring device according to the invention with an amperometric sensor and an arrangement of the generator electrodes 3, 3' outside of the measuring chamber 6. The generator electrodes 3, 3' generating the conditioning agent are arranged at a short distance from the membrane. The conditioning agent can diffuse through the selectively permeable membrane 1 and reach the working electrode, at which it is reduced into the corresponding reducing/oxidising agent. The flow vectors of the conditioning agent formed at the generator electrode are also illustrated. For purposes of simplification, the control device and the generator reference electrode are not included in the figure.

FIG. 4 shows, schematically, a special embodiment of a measuring device according to the invention with amperometric sensor and a module 8 in which the generator electrode 3 is arranged. The conditioning agent generated at the generator electrode diffuses from the module 8 via the connection 7 towards the measuring chamber 6, passes through its selectively permeable membrane 1 and is reduced at the working electrode 2. The flow vectors of the conditioning agent formed at the generator electrode are also illustrated. For purposes of simplification, the control device and the generator reference electrode are not included in the figure.

LIST OF REFERENCE SYMBOLS 1 selectively permeable membrane
2 working electrode
3, 3' generator electrode
4, 5 reference or return electrode
6 measuring chamber
7 connection
8 module with generator electrode

The invention claimed is:

1. Method for cleaning, conditioning, calibration and/or adjustment of an amperometric sensor of a measuring device for determining a content substance in a sample, wherein the measuring device comprises an electrolyte and the amperometric sensor, with a measuring chamber, sealed by a selectively permeable membrane, in which a working electrode and a working reference electrode connected electrically with the working electrode are arranged, and wherein the determination of the content substance takes place during a measuring interval in that a voltage is applied between the working electrode and the working reference electrode, the current which flows via the electrical connection between the working electrode and the working reference electrode is measured and the content substance deduced from the measured current, characterised in that the method comprises the following steps:
generating a conditioning agent at the working electrode and/or at a generator electrode arranged in the measuring device, wherein the conditioning agent is an oxidising or reducing agent,
oxidising the conditioning agent at the working electrode, if the conditioning agent is a reducing agent, or reducing the conditioning agent at the working electrode, if the conditioning agent is an oxidising agent.

2. Method according to claim 1, characterised in that the generator electrode at which the conditioning agent is generated is arranged in the measuring chamber.

3. Method according to claim 1, characterised in that the generator electrode generates the conditioning agent during the measuring interval.

4. Method according to claim 1, characterised in that the conditioning agent is generated during a conditioning interval, wherein the conditioning agent is fed or generated during several conditioning intervals, wherein the conditioning intervals are shorter than the intervals between two consecutive conditioning intervals.

5. Method according to claim 1, characterised in that the conditioning agent is generated continuously.

6. Method according to claim 1 characterised in that a predetermined quantity of conditioning agent is generated.

7. Method according to claim 1 characterised in that the content substance which is to be determined is used as the conditioning agent.

8. Method according to claim 1 characterised in that a detection electrolyte is used as the electrolyte which contains a component which is reduced or oxidised into a detection component through the content substance which is to be determined, wherein the detection component is used as the conditioning agent.

9. Method according to claim 1 characterised in that the content substance which is to be determined is an oxidising agent, selected from the group consisting of oxidative halogen compounds of chlorine, bromine and iodine, chloramines and bromamines, $Cl_2$, $Br_2$, $O_3$, $ClO_2$, peracetic acid, $H_2O_2$, a chlorite or hypochlorite salt or the corresponding acids.

10. Method according to claim 9 wherein the oxidising agent is hypochlorous acid (HOCl).

11. Method according to claim 1 characterised in that an iodide solution is used as electrolyte, wherein iodine is preferably used as conditioning agent.

12. Method according to claim 1 characterised in that an adjustment value is deducted from the current value measured during the measuring interval, wherein the adjustment value is determined in that, during an adjustment interval in which no content substance which is to be determined is present, a voltage is applied between the working electrode and the working reference electrode and the current which flows via the electrical connection between the working electrode and the working reference electrode is measured.

13. Method for calibration and/or adjustment of a measuring device according to claim 1 characterised in that the conditioning agent corresponds to the content substance of the sample which is to be determined, and a defined quantity of conditioning agent is generated in the measuring chamber through electrolysis or a defined of quantity conditioning agent is generated in a section of the measuring device through electrolysis and fed to the measuring chamber, a voltage is applied between the working electrode and working reference electrode and the current which flows via the electrical connection of the working electrode and the working reference electrode is measured.

14. Method according to claim 1 characterised in that the conditioning agent is generated in the measuring chamber through a generator electrode, wherein the generator electrode is operated as the anode if the working electrode is used as the cathode, and operated as the cathode if the working electrode is used as the anode.

15. Method comprising the step of producing a conditioning agent according to the method according to claim 1 and the step of cleaning, conditioning, calibrating and/or adjusting of an amperometric sensor of a measuring device for determining a content substance in a sample with the conditioning agent.

16. Amperometric sensor which can be cleaned, conditioned, calibrated and/or adjusted, wherein the sensor comprises at least one working electrode arranged in a measuring chamber arranged to hold an electrolyte, a working reference electrode and a selectively permeable membrane which limits the measuring chamber, wherein a generator electrode and a generator reference electrode are arranged in the measuring chamber, wherein a control device is provided with which a measuring voltage can be applied between the working electrode and the working reference electrode and with which a generator voltage is applied between the generator electrode and the generator reference electrode, the level of which is different from or equal to that of the measuring voltage, characterised in that the working electrode has at least one cylindrical section and the generator electrode has a hollow cylindrical section, wherein the working electrode is arranged with its cylindrical section within the hollow cylindrical section of the generator electrode.

17. Amperometric sensor which can be cleaned, conditioned, calibrated and/or adjusted, wherein the sensor comprises at least one working electrode arranged in a measuring chamber arranged to hold an electrolyte, a working reference electrode and a selectively permeable membrane which limits the measuring chamber, wherein a generator electrode and a generator reference electrode are arranged in the measuring chamber, wherein a control device is provided with which a measuring voltage can be applied between the working electrode and the working reference electrode and with which a generator voltage is applied between the generator electrode and the generator reference electrode, the level of which is different from or equal to that of the measuring voltage characterised in that the selectively permeable membrane has an effective surface which is smaller than or equal to the surface of the working electrode facing the membrane.

18. Measuring device configured to determine a content substance in a sample and configured to carry out a method for cleaning, conditioning, calibration and/or adjustment of an amperometric sensor of the measuring device, wherein the measuring device comprises an electrolyte and the amperometric sensor, with a measuring chamber, sealed by a selectively permeable membrane, in which the working electrode and a working reference electrode connected electrically with the working electrode are arranged, and wherein the determination of the content substance takes place during a measuring interval in that a voltage is applied between the working electrode and the working reference electrode, the current which flows via the electrical connection between the working electrode and the working reference electrode is measured and the content substance deduced from the measured current, characterised in that the method comprises the following steps:
generating a conditioning agent at the working electrode and/or at a generator electrode arranged in the measuring device, wherein the conditioning agent is an oxidizing or reducing agent,
oxidizing the conditioning agent at the working electrode, if the conditioning agent is a reducing agent, or reducing the conditioning agent at the working electrode, if the conditioning agent is an oxidizing agent,
wherein the device has at least one amperometric sensor and a control device, characterised in that the measuring device has at least one generator electrode arranged in the measuring device.

19. Measuring device according to claim 18, characterised in that the amperometric sensor comprises at least one working electrode arranged in a measuring chamber arranged to hold the electrolyte, a working reference electrode and a selectively permeable membrane which limits the measuring chamber, characterised in that a generator electrode and a generator reference electrode are arranged in the measuring chamber, wherein with the control device a measuring voltage can be applied between the working electrode and the working reference electrode and with which a generator voltage is applied between the generator electrode and the generator reference electrode, the level of which is different from or equal to that of the measuring voltage.

* * * * *

UNITED STATES PATENT AND TRADEMARK OFFICE
CERTIFICATE OF CORRECTION

Page 1 of 1

PATENT NO. : 11,215,579 B2
APPLICATION NO. : 16/429312
DATED : January 4, 2022
INVENTOR(S) : Koppert et al.

It is certified that error appears in the above-identified patent and that said Letters Patent is hereby corrected as shown below:

In the Specification

Column 11, Line 3, after "and" insert the following -- generator electrode arranged therein. --

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*